United States Patent
Birnbaum

(10) Patent No.: US 7,252,089 B1
(45) Date of Patent: Aug. 7, 2007

(54) SURGICAL LAMINAR AIR FLOW APPARATUS AND METHOD

(76) Inventor: Bernardo Birnbaum, 3212 NE. 211 Ter., Aventura, FL (US) 33180

( * ) Notice: Subject to any disclaimer, the term of this patent is extended or adjusted under 35 U.S.C. 154(b) by 88 days.

(21) Appl. No.: 11/251,647

(22) Filed: Oct. 17, 2005

(51) Int. Cl.
*A61F 19/08* (2006.01)

(52) U.S. Cl. .................................... 128/853

(58) Field of Classification Search ............... 128/849, 128/850, 851, 852, 853, 854, 855
See application file for complete search history.

(56) References Cited

U.S. PATENT DOCUMENTS

| | | | | |
|---|---|---|---|---|
| 3,610,238 A | * | 10/1971 | Rich, Jr. ................. | 604/23 |
| 3,763,857 A | * | 10/1973 | Schrading ............... | 128/853 |
| 4,223,669 A | * | 9/1980 | Morledge ................ | 128/847 |
| 4,275,719 A | * | 6/1981 | Mayer .................... | 128/847 |
| 4,950,222 A | * | 8/1990 | Scott et al. ............. | 600/21 |
| 4,998,538 A | * | 3/1991 | Charowsky et al. .... | 128/856 |
| 5,730,153 A | * | 3/1998 | Chang et al. ........... | 128/846 |

* cited by examiner

*Primary Examiner*—Patricia Bianco
*Assistant Examiner*—Camtu Nguyen
(74) *Attorney, Agent, or Firm*—Sanchelima & Assoc., P.A.

(57) ABSTRACT

A apparatus and method for protecting a patient's area from aerobic contamination comprising a flexible drape assembly adhered to the surrounding area being operated on. The drape assembly includes two sheet members having predetermined cooperative dimensions and joined to each other defining an internal cavity with a plurality of outlet openings through the first sheet member. The internal cavity is pressurized with clean filtered air. The apparatus also includes a suction assembly with inlet ports mounted in the proximity of the area being operated on. A non-preferential turbulence free laminar flow is achieved away from the protected exposed area.

6 Claims, 3 Drawing Sheets

SURGICAL LAMINAR AIR FLOW APPARATUS AND METHOD

BACKGROUND OF THE INVENTION

1. Field of the Invention

The present invention relates to a surgical apparatus and method for minimizing infections with aerobic pathogens of an area being operated on.

2. Description of the Related Art

Many infections in patients are contracted during surgical procedures. The surgeons, nurses and other personnel may take some precautionary steps but they are typically not enough to keep bacteria and other organisms away from the open wounds.

Several surgical apparatuses and methods have been developed in the past using different mechanisms to provide air flow in the vicinity of an area to be protected. None of them, however, includes an apparatus that maintains laminar airflow away from the protected area to minimize infection probabilities by aerobic pathogens around the area of surgery.

Applicant believes that one of the closest references corresponds to U.S. Pat. No. 3,610,238 issued to Edward Rich, Jr. on Oct. 5, 1971 for a wound infection prevention device. Rich's patented invention includes a cellular-foam plastic pad encased by a plastic sheet and to which air pressure is fed. The user cuts a hole in the center of the device so that the surgeon can then operate on the patient. In Rich's patented invention the air is directed to the wound, which makes more difficult the surgeon's work.

Applicant believes that another related reference corresponds to U.S. Pat. No. 4,936,318 issued to Schoolman on Jun. 26, 1990 for a vacuum barrier. Schoolman's patented invention is a protective apparatus for preventing the exchange of harmful substances between an area isolated by the apparatus and the environment for use in medical, laboratory, and industrial application and includes a shield, a vacuum barrier, and an adjustable support frame. The apparatus further includes a vacuum source connected to the physical shield to draw air containing solid and liquid matter entrained in the air. Schoolman's patented invention intends to provide protection for persons in proximity to harmful substances such as aerosols produced by surgical procedures at a surgical incision on a patient infected with the AIDS virus or the like.

Applicant believes that another related reference corresponds to U.S. Pat. No. 3,763,857 issued to Schrading on Oct. 9, 1973 for a surgical drape. The patented Schrading's surgical drape includes a an operative area and the fenestrations therein, comprising a fibrous base sheet, a fluid impervious plastic film covering said primary operative area, and an open celled fluid absorbent foam material overlying the plastic film. A reduced air pressure source is connected to suction for removing fluid absorbed in the foam material.

Applicant believes that another related reference corresponds to U.S. Pat. No. 4,275,719 issued to Mayer on Jun. 30, 1981 for an apparatus and method for providing an aseptic surgical environment. In Mayer's patented invention the patient to be operated on is first wrapped with a plastic film sheet, which is adhesively sealed to the patient's body remote from an operating area on the body, and is also sealed against an incision site on the body at the operating area. A sterilized atmosphere is provided beneath the film sheet for contacting the patient's skin. Another sterilized atmosphere is provided within a region substantially adjacent the body including the incision site. The surgeon cuts through the film sheet and into the patient's body.

However, these related references differ from the present invention because they lack a flexible drape assembly of the present invention surrounds the area being operated producing an air flow traveling from the plane of the area being protected to. Also, the present invention includes two sheet members joined to each other and define an internal cavity with a plurality of through outlet openings in the upper sheet member. The present invention provides for a non-preferential flow of filtered air away from the plane of the protected area. One of the sheets is adhered to the patient' The present invention also includes a suction assembly mounted in the proximity of the area being operated on so the airflow circulates from the drape assembly into the surgical room lamp, the user's garment and/or cuff, where a suction assembly is mounted, so the airflow circulates from the drape assembly into the suction assembly is mounted.

Other patents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide an apparatus and method that maintains a laminar air flow away from the exposed area being operated on to minimize infection probabilities.

Still another object is to minimize the exposed area adjacent to the incision from contact with foreign objects.

It is another object of this invention to provide an apparatus and method that has minimized interference with the surgical procedures.

It is yet another object of this invention to provide such apparatus and method that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 2A is a bottom view of the drape assembly represented in the previous figure.

DETAILED DESCRIPTION OF THE PREFERRED EMBODIMENT

Figure 1:
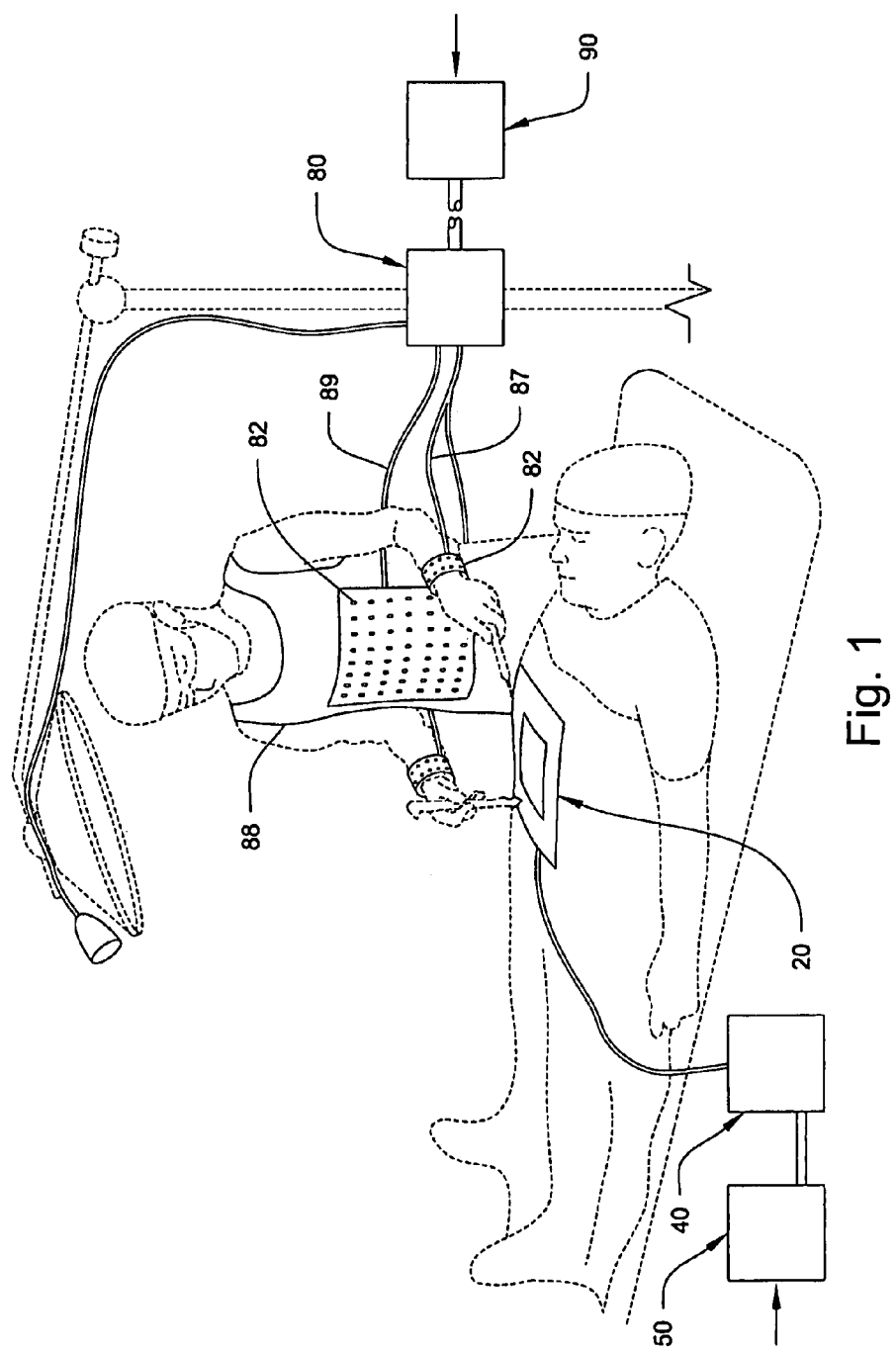
FIG. 1 is a representation of a preferred embodiment for the present invention in use.

Referring now to the drawings, where the present invention is generally referred to with numeral 10, it can be observed that it basically includes flexible drape assembly 20, clean air supply assembly 40, and air suction or partial vacuum assembly 80, as shown in FIG. 1.

Figure 2:
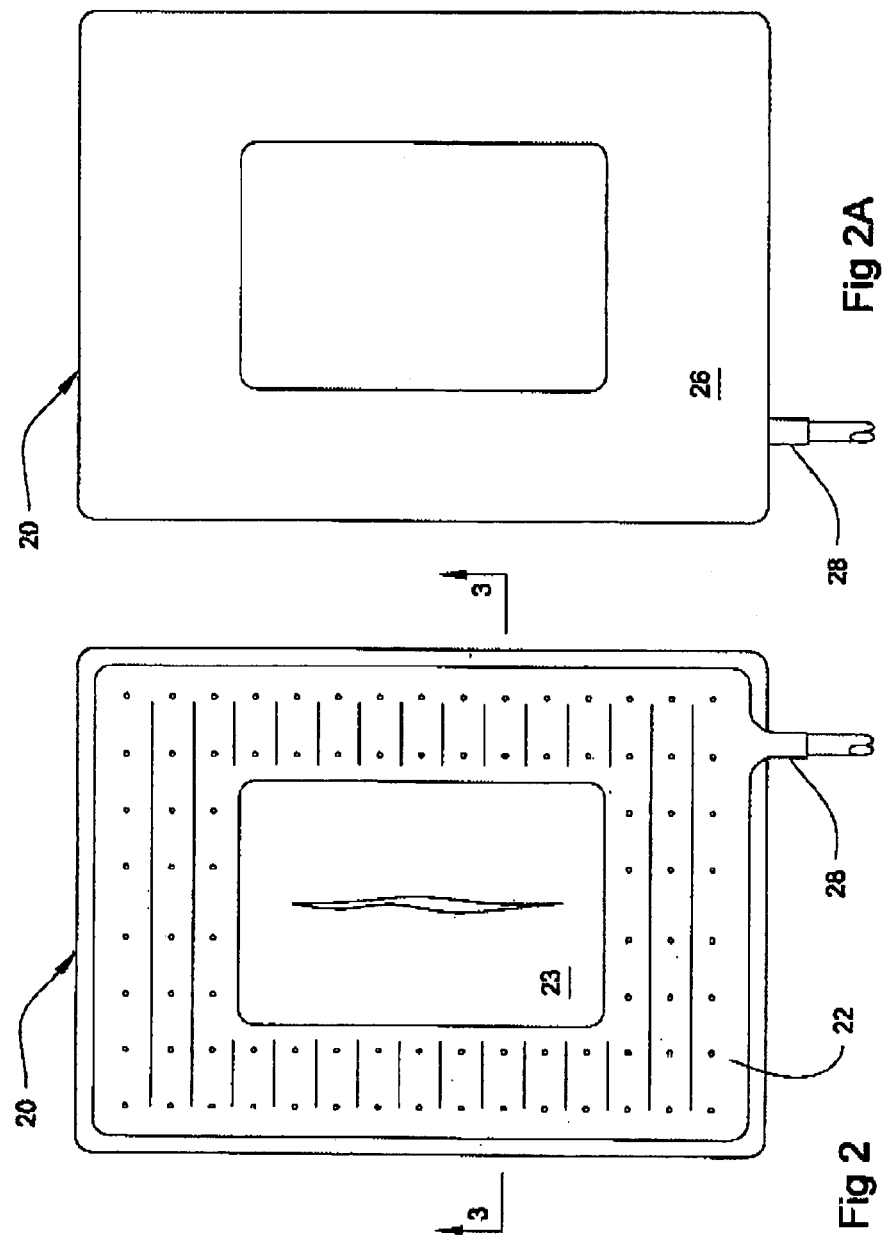
FIG. 2 illustrates a top view of one of the preferred embodiments for the drape assembly used with the invention object of the present application over an area being protected showing a surgical incision.
Figure 3:
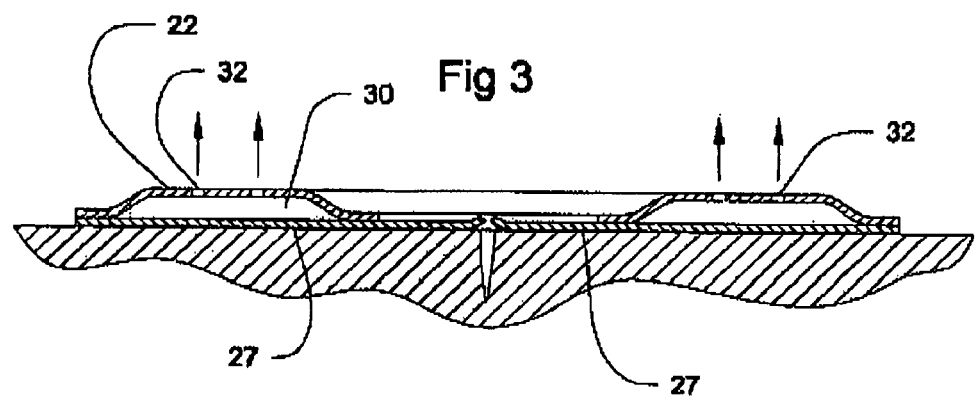
FIG. 3 shows a cross-section of the drape assembly shown in FIG. 2 taken along line 3-3.

In one of the preferred embodiment, flexible drape assembly 20 surrounds the area being operated on, as shown in FIG. 2. Drape assembly 20 includes sheet members 22 and 26 with predetermined cooperative dimensions, as shown in FIG. 3. Drape assembly 20 also has a shape that ergonometrically cooperates with the area being operated on. Sheet members 22 and 26 are peripherally joined to each other defining internal cavity 30. A window 23 is defined by an area where sheet member 22 is missing. A cooperative internal contour of member 22 leaves sheet member 26 by itself in the area referred to as window 23. Sheet member 22 includes a plurality of outlet openings 32. Drape assembly 20 includes an inlet port 28 connected to cavity 30. Sheet member 26 is preferably larger than sheet member 22 and it comes in contact with the patient's body. Sheet member 26 is typically removably mounted to the patient's body with an adhesive 27. Adhesive 27 can also contain an anti-bacterial agent.

Air supply assembly 40 is connected to inlet port 28 and provides pressurized purified air from filter assembly 50 at relatively low pressure to avoid the creation of turbulences. The air is filtered, processed or otherwise sanitized to ensure it is free of pathogens or other substances. The air comes out through outlet openings 32, away from the plane of the area being operated on in a slow laminar, non-preferential flow.

Figure 4:
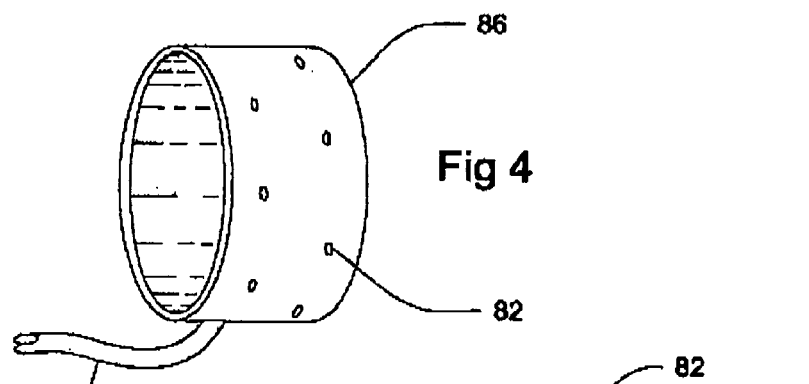
FIG. 4 is an isometric representation of a surgeon's cuff member connected to a vacuum hose.
Figure 5:
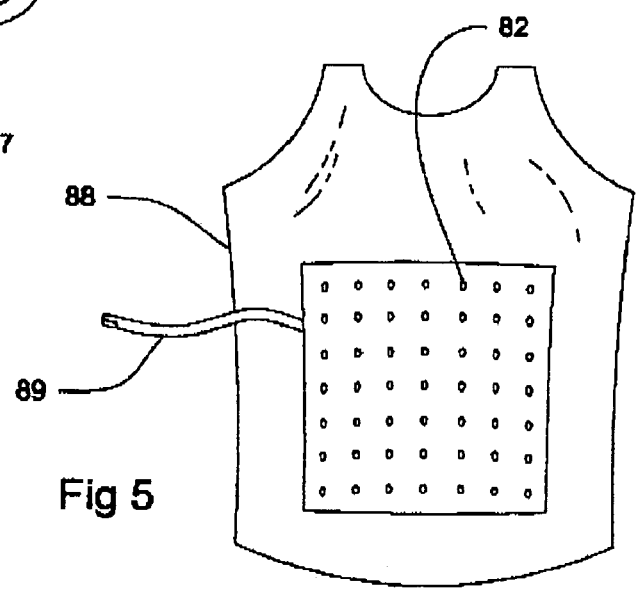
FIG. 5 represents a surgeon's vest or gown connected to a vacuum hose.

Air suction assembly 80 includes inlet ports 82. Air suction assembly 80 is located at a remote inlet ports 82 are mounted in predetermined locations away from outlet openings 32, so that a continuous laminar airflow is induced from outlet openings 32 towards inlet ports 82 providing a negative pressure. Inlet ports 82 are positioned at cooperative locations like the surgical room lamp L, user's garment 86 and/or user's cuff C, as seen in FIG. 1. In FIG. 4 garment 86 is represented partially showing hose 87 that connects it to air suction assembly 80.

The method steps include the preparation of the patient's area to be operated on a protected prior to mounting drape assembly 20. The positioning of drape assembly 20 is such that a laminar, non-preferential air flow is produced away from the plane of the protected area. A negative air pressure or partial vacuum is produced at cooperative locations remotely from drape assembly 20 to ensure that the path of the air flow is away from the protected area. The magnitudes for the pressurized air and the partial vacuum are selected so that turbulences are avoided.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. An apparatus for protecting a surgical area of a patient from aerobic contamination comprising:
   A) a flexible drape assembly having first and second sheet members kept at a spaced apart and parallel relationship with respect to each other having predetermined cooperative dimensions and joined to each other defining an internal cavity with a plurality of outlet openings through said second sheet member, and a cooperative window area being defined where said first sheet member does not correspond with said second sheet member, said drape assembly further including a first inlet port connected to said cavity;
   B) means for supplying pressurized purified air to said inlet port; and
   C) means for suctioning air having at least one second inlet port at a remote predetermined distance from said outlet openings so that continuous laminar airflow is established from said outlet openings towards said second inlet ports.

2. The apparatus set forth in claim 1, wherein said drape assembly surrounds the area being operated on and said second sheet member includes adhesive means.

3. The apparatus set forth in claim 2 wherein said adhesive means includes an anti-bacterial agent.

4. The apparatus set forth in claim 3, wherein said at least one second inlet port is mounted to the surgical room lamp.

5. The apparatus set forth in claim 3, wherein said at least one second inlet port is mounted to a user's garment.

6. The apparatus set forth in claim 3, wherein said at least one second inlet port is mounted to a user's cuff.

* * * * *